(12) United States Patent
Boberschmidt et al.

(10) Patent No.: US 6,570,363 B2
(45) Date of Patent: *May 27, 2003

(54) MEDICALLY IMPLANTABLE ENERGY STORAGE SYSTEM HAVING SAFE RECHARGING CAPABILITIES

(75) Inventors: Werner Boberschmidt, Ismaning (DE); Hans Leysieffer, Taufkirchen (DE)

(73) Assignee: Cochlear Limited, Lane Cover (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/824,212

(22) Filed: Apr. 3, 2001

(65) Prior Publication Data

US 2001/0026144 A1 Oct. 4, 2001

(30) Foreign Application Priority Data

Apr. 3, 2000  (DE) .......................... 100 16 520

(51) Int. Cl.⁷ .......................... H02J 7/00; A61N 1/378
(52) U.S. Cl. ...................................... 320/122
(58) Field of Search .................. 607/33, 61, 55; 320/137, 136, 122

(56) References Cited

U.S. PATENT DOCUMENTS

| | | | | |
|---|---|---|---|---|
| 4,658,358 A | * | 4/1987 | Leach et al. | 73/865.1 |
| 5,411,537 A | | 5/1995 | Munshi et al. | 607/33 |
| 5,690,693 A | * | 11/1997 | Wang et al. | 607/61 |
| 5,702,431 A | | 12/1997 | Wang et al. | 607/161 |
| 5,713,939 A | | 2/1998 | Nedungadi et al. | 607/133 |
| 6,100,664 A | * | 8/2000 | Oglesbee et al. | 320/125 |
| 6,137,265 A | * | 10/2000 | Cummings et al. | 320/133 |
| 6,358,281 B1 | * | 3/2002 | Berrang et al. | 607/57 |

* cited by examiner

*Primary Examiner*—Edward H. Tso
*Assistant Examiner*—Pia Tibbits
(74) *Attorney, Agent, or Firm*—Nixon Peabody LLP; David S. Safran

(57) ABSTRACT

An implantable energy storage arrangement for a medical implant, which is provided with a rechargeable storage for electrical energy and a unit for controlling the charging process via an actuator in the charging path. A control which can be externally activated is provided to bypass the actuator. Furthermore, a corresponding process for operating an implantable energy storage arrangement provides for bypassing of the actuator when storage voltage is overly low.

20 Claims, 1 Drawing Sheet

MEDICALLY IMPLANTABLE ENERGY STORAGE SYSTEM HAVING SAFE RECHARGING CAPABILITIES

BACKGROUND OF THE INVENTION

1. Field of the Invention

This invention relates to an implantable energy storage arrangement for a medical implant, the energy storage arrangement comprising a rechargeable storage for electrical energy and a unit for controlling the charging process via an actuator in the charging path. This invention further relates to a process for operating an implantable energy storage arrangement for a medical implant, said energy storage arrangement comprising a rechargeable storage for electrical energy, wherein during normal operation the charging process is controlled by means of a control unit via an actuator in the charging path.

2. Description of Related Art

Energy storage arrangements and processes of the aforementioned type are described, for example, in commonly owned, co-pending U.S. patent application Ser. No. 09/311,566 which is hereby incorporated by reference, and U.S. Pat. Nos. 5,411,537, 5,702,431 and 5,713,939. Conventionally, the implantable energy storage arrangements are recharged transcutaneously via an inductive path by means of an external charging device. The charging device conventionally is controlled by measuring the charging current and the voltage of the storage by means of a control unit and by converting the same into the corresponding control pulses for a switch in the charging circuit, wherein a suitable charging program is used.

When the energy storage is in operation, two undesirable operating states can occur: On the one hand, overcharging of the battery can occur if the charging process is not terminated at the proper time, which may lead to gas evolution with subsequent destruction of the storage. On the other hand, when charging of the storage is not done on time, the storage voltage may drop to values which are below a minimum operating voltage which is necessary for defined operation or optionally for limited function of the implant which is to be supplied by the energy storage. In the latter case, the storage voltage may possibly drop to such an extent that even sufficient voltage supply of the implant-side electronics to control the charging process is no longer ensured. Often, the control electronics comprise a microprocessor system in which, in the case of undervoltage, wrong logic operations can occur or the contents of volatile memories can be lost. Thus, in the case of undervoltage, in these systems proper charge control is no longer ensured; this can lead to the charging path being switched to high resistance by a microprocessor malfunction when it enters the undervoltage range, whereby charging of the storage is permanently prevented.

SUMMARY OF THE INVENTION

A primary object of this invention is to devise an implantable energy storage arrangement for a medical implant and a process for its operation, wherein safe recharging of the energy storage is possible even when the storage is completely discharged or has been discharged at least to such an extent that the storage voltage has dropped below the normal voltage range for the control unit.

This object is achieved in conformity with the invention by an implantable energy storage arrangement for a medical implant, with a rechargeable storage for electrical energy and a unit for controlling the charging process via an actuator in the charging path, characterized in that there is a means which can be externally activated to bypass the actuator. The above object furthermore is achieved in conformity with the invention by a process for operating an implantable energy storage arrangement for a medical implant, with a rechargeable storage for electrical energy, in normal operation the charging process being controlled by means of a control unit via an actuator in the charging path, wherein when it is not possible to charge the storage via the actuator due to overly low storage voltage, a bypass means provided in the implantable energy storage arrangement is activated from the outside to bypass the actuator.

In this approach in accordance with the invention, it is advantageous that even when discharge of the storage has progressed far or even the storage has been completely discharged, i.e., at very low storage voltages, the rechargeability of the storage is ensured at any time by preventing blockage of the charging path due to malfunction of the control unit caused by the undervoltage, which blockage is prevented by having the possibility of means of bridging the actuator element in the charging path by external actuation of the bridging unit.

These and further objects, features and advantages of the present invention will become apparent from the following description when taken in connection with the accompanying drawing which, for purposes of illustration only, shows an embodiment in accordance with the present invention.

BRIEF DESCRIPTION OF THE DRAWINGS

The single FIGURE is a block diagram of an implantable storage arrangement for a medical implant in accordance with the invention.

DETAILED DESCRIPTION OF THE INVENTION

Figure 1:
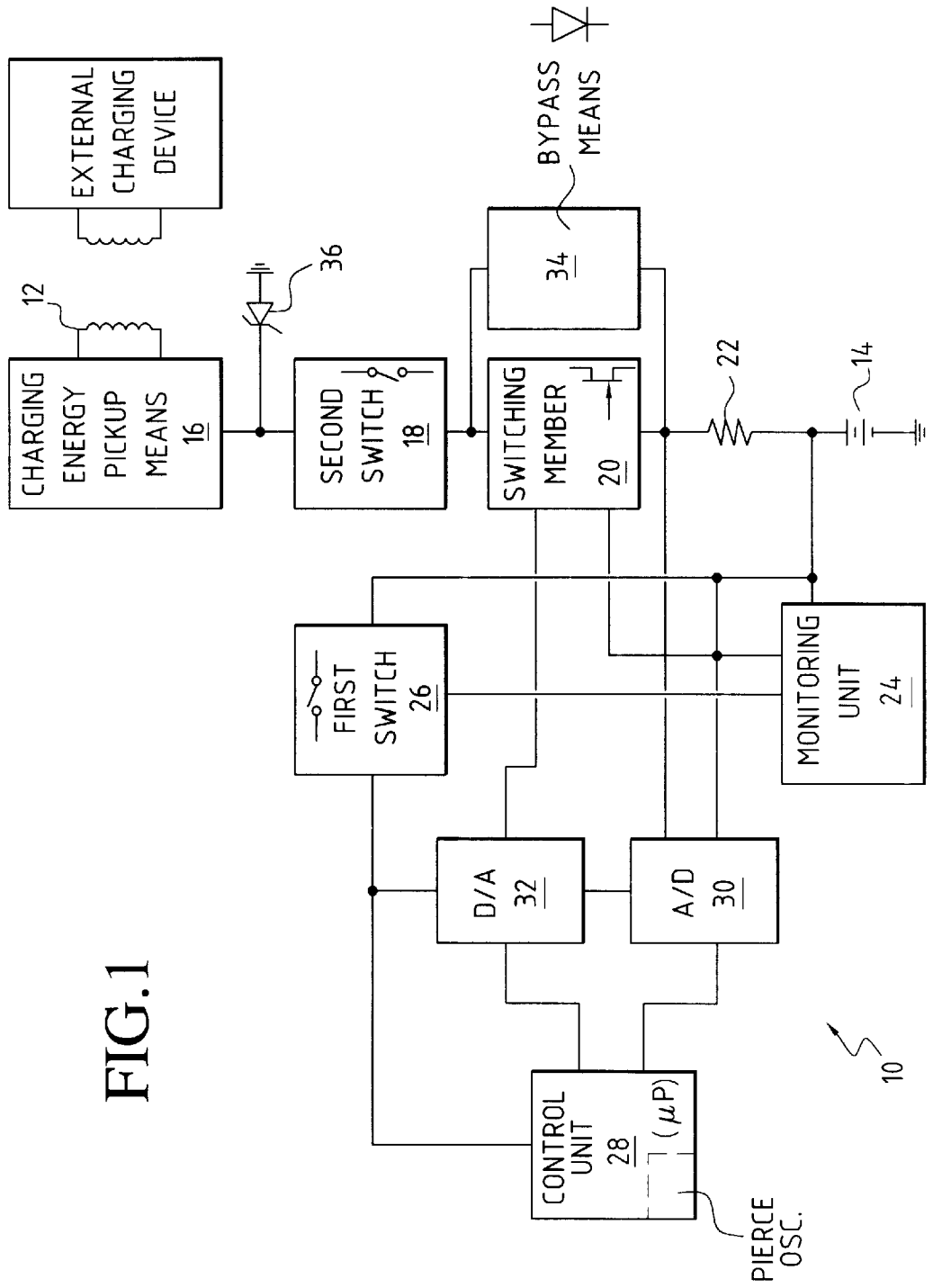

The sole FIGURE schematically shows the wiring of the essential elements of an implantable storage arrangement 10 which is used as the power supply for a medical implant which can be, for example, a fully implantable hearing system for direct mechanical stimulation of the middle ear or inner ear or electrical stimulation of the inner ear. A charging coil 12 is used to pick up the electrical energy which has been inductively transmitted transcutaneously by an external charging device (not shown) and to feed power into the charging path of a rechargeable energy storage 14 which can be for example a NiMH battery. The voltage induced in the charging coil 12 by the external charging device is rectified and conditioned in a unit 16. A Zener diode 36 protects the electronic components which are at the charging voltage potential against an excessive charging voltage.

The charging current flows to the battery 14 through a mechanical switch 18 which is closed in normal operation, through a control and switching element 20 which is preferably essentially a FET and which acts as a controllable resistor in the charging current path, and through a shunt resistor 22. A monitoring unit 24 is connected directly to the battery 14 and is used to sense and monitor the battery voltage. On the output side the monitoring unit 24 is connected on the one hand to the control and switching element 20 and on the other to the switch 26 via which a microprocessor system 28 is connected to the battery 14 which acts as the voltage supply. The microprocessor system 28 is clocked preferably by a Pierce oscillator (not shown). An A/D converter 30 is used to measure the voltage of the battery 14 and the voltage drop across the shunt resistor 22, in which manner the two most important parameters when the battery 14 is being charged, specifically the battery voltage and the charging current, can be measured. The A/D converter 30 outputs these values as an input signal to the microprocessor system 28 which depending on the sensed battery voltage and the sensed charging current controls via a D/A converter 32 the control/switching element 20, and thus, the charging current or the charging voltage, respectively, in conformity with a predetermined charging strategy. In particular, a monitoring function is implemented in a conventional manner, which monitoring function provides for the charging process to be terminated after a predetermined charging termination criterion is reached by switching the control/switching element 20 to high resistance.

To prevent excess discharging of the battery 14 in operation, the energy storage arrangement 10 is conventionally provided with a function which timely warns the implant wearer of discharge of the battery 14 in order to encourage him to undertake a charging process. If recharging does not take place because, for example, the implant wearer is prevented from doing so, the battery voltage can drop below the allowable lower limit. As soon as the monitoring unit 24 ascertains that the sensed battery voltage has fallen below a predetermined lower threshold, the monitoring unit 24, on the other hand, turns off the microprocessor 28 by opening the switch 26 interrupting the voltage supply thereof. This ensures that the microprocessor 28 is not operated at power supply voltages which are so low that the microprocessor 28 can execute incorrect logic operations or can lose the contents of volatile memories. This is ensured by correspondingly selecting the lower voltage limit. On the other hand, the monitoring unit 24 sets the control/switching element 20 into a conductive state when the voltage falls below the lower voltage limit to ensure that charging of the battery 14 is also possible at any time in the undervoltage range and blockage of the charging path by malfunction of the microprocessor 28 is prevented. As an additional effect, turning off the microprocessor 28 results in the power consumption of the electronics being reduced to the power consumption of the monitoring unit 24 which is only some 100 nA in practice. This has the benefit that the battery 14 is less loaded and thus the time interval to complete discharge of the battery 14 is lengthened; this reduces the risk of complete discharge.

In a charging process which is undertaken in the undervoltage range the voltage of the battery 14 gradually increases. After the battery voltage has exceeded the predetermined lower voltage threshold of the monitoring unit 24 by the value of hysteresis, the monitoring unit 24 again turns on the microprocessor system 28 by closing the switch 26, by which the microprocessor system begins to control and monitor the charging process in the above described manner. In this way, the control of the control/switching element 20 is transferred from the monitoring unit 24 to the microprocessor system 28. By suddenly turning on the power supply voltage by closing the switch 26, a steep voltage rise is accomplished which reliably ensures stimulation of oscillations of the Pierce oscillator of the microprocessor system 28.

Furthermore, the monitoring unit 24 is designed such that, when the sensed battery voltage exceeds a predetermined maximum value, the control/switching element 20 is switched into a non-conductive state to prevent overcharging of the battery 14 even when the microprocessor system 28 due to an error does not terminate the charging process after reaching the predetermined charging termination criterion.

The mechanical switch 18 is designed in the conventional manner such that it responds to mechanical expansion of the battery 14 as occurs in case of excess gas evolution which accompanies overcharging, and interrupts the charging path or prevents reception of charging energy to prevent further charging of the battery 14.

In this way, three independent monitoring circuits are implemented in the described storage arrangement 10, which monitoring circuits terminate the charging of the battery at the proper time to prevent damage. It is primarily the microprocessor system 28 which terminates the charging process when a predetermined charging termination criterion is reached. Independent therefrom, the monitoring unit 24 terminates the charging process when the battery voltage sensed by it independently of the microprocessor system 28 exceeds a predetermined maximum value. Finally, when the first two monitoring circuits fail the mechanical switch 18 timely terminates the charging process independently of the electronics such that damage of the battery 14 and hazard to the implant carrier are reliably prevented.

Furthermore, the monitoring unit 24, independently of the microprocessor system 28, detects threatening excess discharging of the battery 14, and malfunctions of the microprocessor system 28 which may result therefrom are prevented by turning off the microprocessor system. Furthermore, in this case, the monitoring unit 24 assumes control of the charging path, whereby, independently of the microprocessor system 28, in the undervoltage range, it is always ensured that the charging path is conductive so that recharging of the battery 14 is possible at any time. Besides, by suddenly again turning on the power supply voltage of the microprocessor 28 by the closing of the switch 26 by means of the monitoring unit 24, start-up problems of the Pierce oscillator of the microprocessor system 28 can be prevented.

A bypass means 34 is connected in parallel to the control/switching element 20 and can be actuated externally, i.e., from outside the body, in order to bypass or short-circuit the control/switching element 20. The bypass means 34 is provided for the case in which the storage 14 is discharged such that the storage voltage has dropped to such an extent that it is no longer sufficient for proper operation of the monitoring unit 24. Here, the case can arise that the control/switching element 20 assumes a resistance which is so high that it does not enable charging of the storage 14 via the normal charging path. In this case, by actuating the bypass means 34 it is possible to intervene from the outside to bypass the control/switching element 20 and thus enable reliable charging of the storage 20 even in case of an extreme undervoltage or complete discharge.

The bypass means 34 can be formed, for example, by a mechanical switch which can be closed by means of an external magnet (Reed switch), and the magnet can preferably be integrated into the external charging device. In this case, when the charging device is held on the skin of the implant wearer, the switch 34 is closed and charging is possible via the current path through switch 34. But, as soon as the storage voltage is sufficient again, for reliable operation of the monitoring unit 24, the switch 34 should be opened again by removing the magnet in order to re-activate the above described normal charging function and especially to prevent overcharging.

In an alternative embodiment, the bypass means 34 can also be formed by a diode which is poled in the reverse direction, for example a Zener diode. The reverse voltage of the diode is dimensioned such that it is above the charging voltages which occur in the normal charging mode and thus does not influence the normal charging process, but is below the reverse voltage of the protective diode 36. In an emergency, i.e., when the storage voltage is no longer sufficient for operation of the monitoring unit 24, a special external emergency charging device is used at the start of recharging, which external emergency charging device differs from the external charging device which is used for the normal charging process essentially in that it provides for a charging voltage to be produced which is much higher than in a normal charging process and above the reverse voltage of the bridging diode 34, but below the reverse voltage of the protective diode 36. In this way, bridging of the control/switching element 20 is achieved by the emergency charging device. Instead of using a special emergency charging device, the normal charging device can also be provided with a switchable emergency charging mode. However, when a storage voltage is reached which again is sufficient for reliable operation of the monitoring unit 24, the emergency charging mode should be terminated to again block the bridging diode 34, and thus, to re-activate the normal charging function and especially to prevent overcharging.

By means of the bypass unit 34 it is thus ensured that recharging by external activation is possible even when the storage 14 is completely discharged.

We claim:

1. An implantable energy storage arrangement for a medical implant, comprising a rechargeable storage device that stores electrical energy;
   a control unit that controls the charging of the rechargeable storage device via an actuator in a charging path; and an externally activatable bypass means for bypassing the actuator.

2. The storage arrangement of claim 1, wherein the bypass means is a magnetically actuateable switch.

3. The storage arrangement of claim 1, wherein the bypass means is a diode which is poled in the reverse direction and which has a reverse voltage that is greater than charging voltages which occur in a normal charging process.

4. The storage arrangement of claim 3, further comprising a protective diode for the control unit, the reverse voltage of the protective diode being greater than that of the bypass diode.

5. The storage arrangement of claim 1, wherein the actuator comprises a controllable resistance.

6. The storage arrangement of claim 1, further comprising a monitoring unit which is independent of the control unit and which senses a rechargeable storage device voltage independently of the control unit and is operable to assume control of the charging path when the sensed storage device voltage lies outside a predetermined range.

7. The storage arrangement of claim 6, wherein the monitoring unit is operable for switching the charging path such that a charging current can be supplied to the storage device when the sensed storage device voltage falls below a predetermined first lower threshold.

8. The storage arrangement of claim 7, wherein the monitoring unit is operable for making the actuator conductive when the storage device voltage sensed by the monitoring unit falls below a predetermined first lower threshold.

9. The storage arrangement of claim 8, wherein the control unit comprises a microprocessor system which is supplied with voltage from the storage device via a first switch, the monitoring unit capable of cutting off the microprocessor system from voltage supplied by the storage device by opening a first switch when the sensed storage voltage falls below a predetermined second lower threshold.

10. The storage arrangement of claim 9, wherein the first and the second lower thresholds are identical.

11. The storage arrangement of claim 9, wherein the monitoring unit is adapted to connect the microprocessor system to the voltage supplied by the storage device, by closing the first switch when the sensed storage device voltage exceeds a predetermined first upper threshold and to transfer control of the controllable resistance to the microprocessor system.

12. The storage arrangement of claim 9, wherein the microprocessor system is clocked by a Pierce oscillator.

13. The storage arrangement of claim 8, wherein the control unit comprises means for sensing the storage device voltage and current in the charging circuit, and for controlling the actuator according to a charging program as a function of sensed values.

14. The storage arrangement of claim 6, wherein the monitoring unit is adapted to switch the charging path such that charging current is prevented from flowing to the storage, when the storage device voltage exceeds a predetermined maximum value.

15. The storage arrangement of claim 14, wherein the monitoring unit is adapted to make the controllable resistance non-conductive when the storage device voltage exceeds a predetermined maximum value.

16. The storage arrangement of claim 1, comprising a second switch which is responsive to mechanical changes of the storage device due to overcharging so as to decouple the storage from a charging current source or prevent reception of charging energy.

17. The storage arrangement of claim 16, wherein the second switch is responsive to expansion of the storage device so as to interrupt a charging current path or to prevent reception of charging energy.

18. The storage arrangement of claim 1, comprising means for receiving charging energy which is inductively transmitted transcutaneously from an external source and for conditioning the charging energy.

19. The storage arrangement of claim 1, wherein the medical implant is a fully implantable hearing system.

20. A process for operating an implantable energy storage arrangement for a medical implant, said energy storage arrangement comprising a rechargeable storage device for electrical energy, wherein during normal operation, charging is controlled by means of a control unit via an actuator in a charging path, and wherein when it is not possible to charge the storage via the actuator due to overly low storage voltage, bypass means provided in the implantable energy storage arrangement is externally activated to bypass the actuator.

* * * * *